United States Patent [19]

Landa

[11] Patent Number: 4,626,684
[45] Date of Patent: Dec. 2, 1986

[54] RAPID AND AUTOMATIC FLUORESCENCE IMMUNOASSAY ANALYZER FOR MULTIPLE MICRO-SAMPLES

[76] Inventor: Isaac J. Landa, 12109 Greenleaf Ave., Potomac, Md. 20854

[21] Appl. No.: 513,307

[22] Filed: Jul. 13, 1983

[51] Int. Cl.[4] ............................................. G01T 1/00
[52] U.S. Cl. ............................... 250/328; 250/461.1; 250/461.2
[58] Field of Search .............................. 356/317, 318; 250/461.2, 372, 328, 458.1, 461.1; 350/96.18

[56] References Cited

U.S. PATENT DOCUMENTS

| | | | |
|---|---|---|---|
| 3,854,050 | 12/1974 | Peterson et al. | 250/328 |
| 3,992,631 | 11/1976 | Harte | 250/461.2 |
| 4,037,961 | 7/1977 | Macemon | 356/318 |
| 4,208,094 | 6/1980 | Tomlinson, III et al. | 350/96.18 |
| 4,318,615 | 3/1982 | Sagusa et al. | 250/328 |
| 4,501,970 | 2/1985 | Nelson | 250/458.1 |

OTHER PUBLICATIONS

American Instrument Co., Inc. Bulletin 2423-1 Silver Spring, Md. 20910 (1968).
Brinkmann/Organon Microtiter Plate Reader/Colorimeter Brochure.
Roger A. Munsinger, "Fiber-Optic Colorimetry," Brochure.
The Titertek Multiscan Operating Instructions.
MicroFLUOR Reader Exerpt from a Catalogue.
Dynatech Laboratories, "The Sensitivity and Precision of the Microfluor System".
C. A. Parker, "Photoluminescence of solutions," Elsivier Publishing Co. (1968).
A. M. Deelder et al., "Automated Measurement of Immunogalactosidase Reactions with a Fluorogenic Substrate by the Aperture Defined Microvolume Measurement Method and its Potential Application to Schistosoma Mansoni Immunodiagnosis," Journal of Immunological Methods, vol. 36, pp. 269-283, (1980).
Instrumentation Laboratory Brochure "New, Computer-Controlled IL Multistate III Micro Centrifugal Analyzer," etc.
R. M. Nakamura, MD, "Fluorescent Antibody Methods: Quality Assurance Procedures", Immunoassays in the Clinical Laboratory, pp. 149-172, 1979.
R. M. Nakamura, MD, "Recent Advances in Immunochemical Fluorescent Analytical Methods," Immunoassays in the Clinical Laboratory, pp. 211-226, 1979.
Abraham Shalev et al., "Detection of Attograms of Antigen by a High-Sensitivity Enzyme-Linked Immunoabsorbent Assay (HS-ELISA) Using a Fluorogenic Substrate," Journal of Immunological Methods, pp. 125-139, 1980.
Robert H. Yolken et al., "Enzyme-Linked Fluorescence Assay: Ultrasensitive Solid-Phase Assay for Detection of Human Rotavirus," Journal of Clinical Microbiology, pp. 317-321, Sep. 1979.
K. W. Walls et al., "Titration of Human Serum Antibodies to Toxoplasma Gondii with a Simple Fluorometric Assay," Journal of Clinical Microbiology, pp. 234-235, Feb. 1978.
T. P. Gillis, "Quantitative Fluorescent Immunoassay of Antibodies to, and Surface Antigens of *Actinomyces viscosus*," Journal of Clinical Microbiology, pp. 202-208, Feb. 1978.

*Primary Examiner*—Janice A. Howell
*Attorney, Agent, or Firm*—Finnegan, Henderson, Farabow, Garrett & Dunner

[57] ABSTRACT

An apparatus uses a rapid and efficient method for conducting fluorescence measurements, such as immuno assay, of a plurality of samples of a substance using pulsed or continuous light energy, front-end fluorescent optics, a mechanism which allows for lateral and tranverse scanning of rows and columns of wells, and spectra emission analysis of the spectra from the excited samples.

22 Claims, 11 Drawing Figures

RAPID AND AUTOMATIC FLUORESCENCE IMMUNOASSAY ANALYZER FOR MULTIPLE MICRO-SAMPLES

BACKGROUND OF THE INVENTION

The present invention relates to a fluorescence analyzer which operates rapidly and provides automatic measurements of a large number of samples.

In the research environment fluorescence measuring apparatus can be used for organic and inorganic identifications of compounds and for the study of molecular structures. It is applied to the study of enzyme mechanisms and kinetics, polypeptide derivative and synthesis studies, polymer properties, development of new dye and stain techniques, biological pathways and interactions.

In clincial analysis such apparatus is used for measurements in immunoserology, microbiology, toxicology, clinical chemistry, histopathology, and coagulation.

In the industrial and agricultural area fluorescence measuring apparatus can be used for toxic assays and contamination studies. This apparatus can be used for quality control and contamination studies in food processing and provides measurements appropriate to chemical applications useful to toxic studies, mutagenic and carcinogenic assays, polymer chemistry, purity analysis as well as chromotography techniques and organic and inorganic molecular analysis.

In the fermentation area it is used in enzyme immobilization and purity analysis. In the pharmaceutical area its applications are enzyme systems analysis, drug effect studies, amino acid analysis and pharmacological monitoring. In veterinary medicine it can be used for diagnostic monitoring, toxin studies, monitoring for pharmacology studies and breeding verifications.

In environmental applications, it can be used for inorganic and organic pollution monitoring, toxin studies, microbial assays and carcinogenic assays, and in the petrochemical industry its applications include carcinogenic and contamination studies, refining assays and quality control.

One powerful discipline is the immunalogical studies. In recent years, new immunological methods have been developed in which plates having a plurality of wells for holding samples (one type of such carrier is the "MICROTITER" plate); and are coated with the specific antigen, incubated further with the specific antibody with or without the addition of an "unknown" amount of the same antigen, and subsequently, a second antibody, directed against the first antibody, is added. The latter antibody is conjugated to an enzyme such as peroxidase or alkaline phosphatase. The amount of enzyme immobilized on the microtiter plate is determined by the addition of the proper substrate. The colorimetric reaction is measured by a spectrophotometer which is designed to accomodate microtiter plates.

An alternative method is to coat the plates first with the specific antibody, then add enzyme-labeled antigen as a second layer plus an "unknown" antigen, and finally, add the enzyme substrate as described above. The same type of measurement is then made by the spectrophotometer. This measurement method is called the enzyme immunoassay (EIA) or the enzyme-linked immunosorbent assay (ELISA).

The EIA and ELISA detection methods are highly sensitive and compare with other chemical methods such as high-pressure liquid chromatography and radioimmunoassay methods used in the prior art. The EIA assay is as specific as the antibody used. If the antibody is extremely specific, then the assay will also be extremely specific. For example, a highly specific antibody will not cross-react with other antigens, e.g., antibodies specific for native DNA will not cross react with single-stranded DNA.

The EIA assay has been used to detect hormones and in many instances has replaced with equal or better sensitivity the radioimmunoassay methods for hormone detection. The EIA assay also is used to detect immunoglobulins, carcinogenic antigens, infectious disease and viral infections. Rubella antigens, EB virus, measles, herpes viruses and others are examples of viral antigens already detected by EIA. EIA assay methods have found utilization in veterinary and agricultural applications. Future applications will involve the detection of auto-immune diseases, transplantation antigens, and virtually any compound which is being assayed currently by chemical methods or by radioimmunoassay.

Even though the EIA assay method has provided highly sensitive and rapid measurement capabilities, the current instruments used are essentially colorimeters, and thus limit the choice of substrates to those that produce color reactions. Even though other substrates are available which may be many times more sensitive, no instruments were available which could use such substrates. By using a fluorescent substrate a further increased sensitivity of manyfold over that of using a colorimetric substrate, has been observed. In some cases, measurement of antigen levels 1,000 fold smaller than can now be detected on the same microtiter plate, could be detected using a fluorescence substrate. The present invention is an apparatus which can measure the fluorescence of the enzyme substrate complex directly in the microtiter plates.

SUMMARY OF THE INVENTION

The present invention overcomes the problems and disadvantages of the prior art by using fluorescent measurement with a microtiter plate apparatus thereby achieving rapid and sensitive analysis. The rapidity and sensitivity of measurement makes the fluorescence analyzer of the present invention practical in the clinical environment to detect virological and bacteriological disease at early states of the disease.

The fluorescence analyzer of the present invention is highly sensitive, thus allowing for the identification of very low concentration compounds. Its speed and sensitivity enables the measurement of microsamples in a matter of seconds. It can be used for the above applications including research, clinical analysis and industrial and agricultural measurements.

In accordance with the purpose of the invention, as embodied and broadly described herein, the fluorescence measuring apparatus comprises excitation means for producing light energy; front end fluorescent optics which direct the excitation light energy on a path orthogonal to the surface of the substance being measured and which also receives fluorescent emission spectra back along substantially the same path from the substance; means for scanning the front end fluroescent optics from sample to sample of a plurality of samples; and spectra emission analyzing means for receiving fluorescent emission spectra from the excited samples of the substance through the front end fluorescent optics.

The emission analyzing means detects the light intensity at the measured wavelength of the fluorescent emission spectra.

DESCRIPTION OF THE PREFERRED EMBODIMENT

Reference will now be made in detail to the present preferred embodiment of the invention, an example of which is illustrated in the accompanying drawings.

Figure 1A:
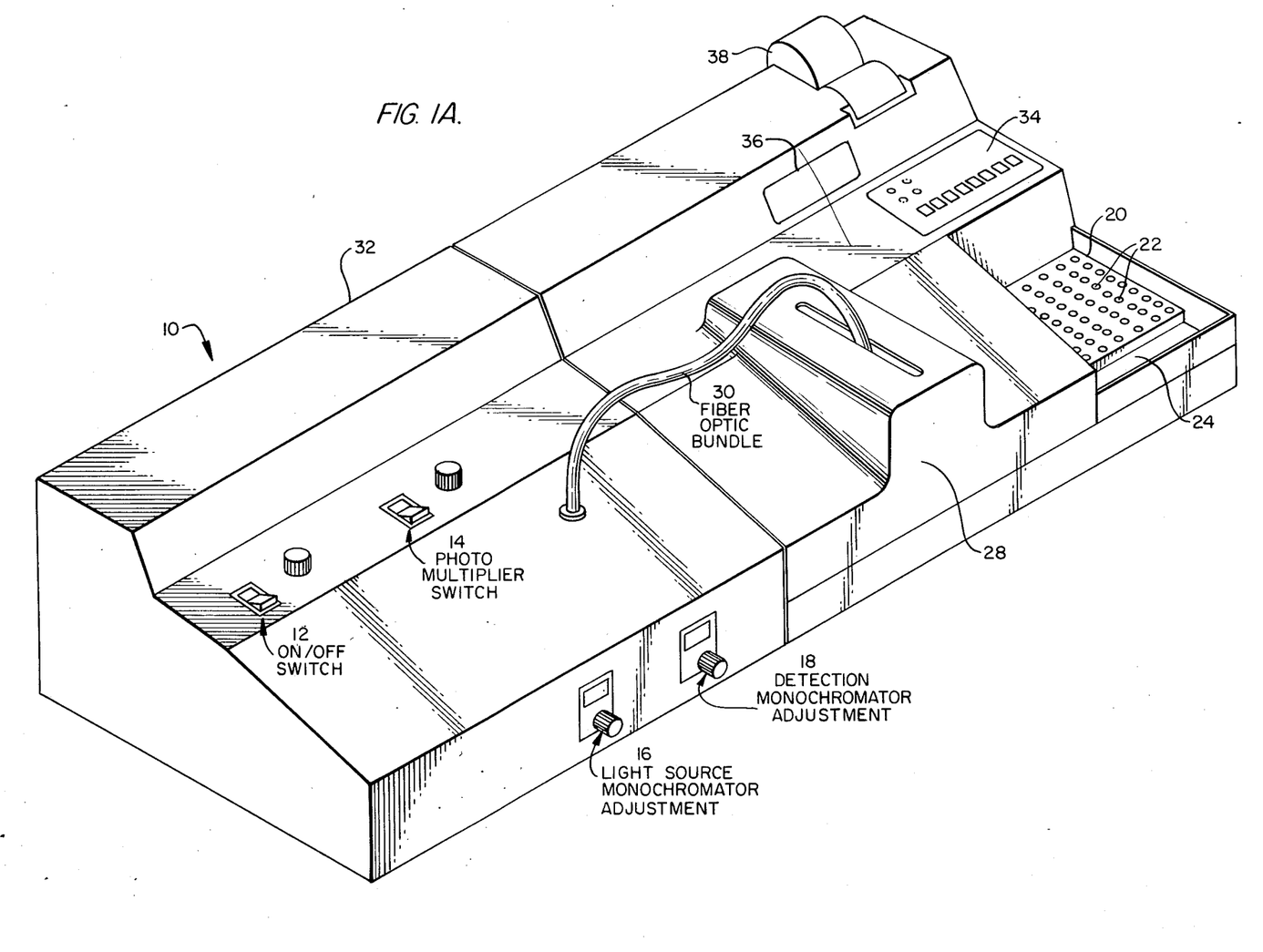
FIG. 1A is a perspective view of one embodiment of the fluorescence measuring apparatus of this invention.

A preferred embodiment of the fluorescence measuring apparatus is shown in FIG. 1A, and is represented generally by 10. FIG. 1A shows one suggested external appearance of a fluorescence instrument. A power switch 12 is used to energize the instrument and photomultiplier switch 14 energizes the light detection. Controls 16 and 18 respectively, are used to adjust the light source monochromator and the detection monochromator.

A plate 20 having a plurality of wells 22 is mounted on movable carrier means 24. It will be understood that means other than a microtiter plate can be used to carry samples of the material under investigation. The carrier means 24 moves on a track mechanism for rapid movement under the scanning mechanism enclosed in section 28 of the fluorescent EIA apparatus 10. Fiber optic bundle 30 has one end connected to the scanning mechanism and the other end to section 32 of the apparatus which encloses the light source and detection source.

Panel 34 has controls for the operation of the fluorescent immuno assay apparatus which include reference measurements, normalization to a reference measurement, advancement controls for the plate and for the scanning mechanism, display and print controls, control function and status indicators, and parameter input controls.

Range display 36 shows the preset range for measurement of fluorescence. Results of the measurement are printed out on paper roll 38.

Figure 1B:
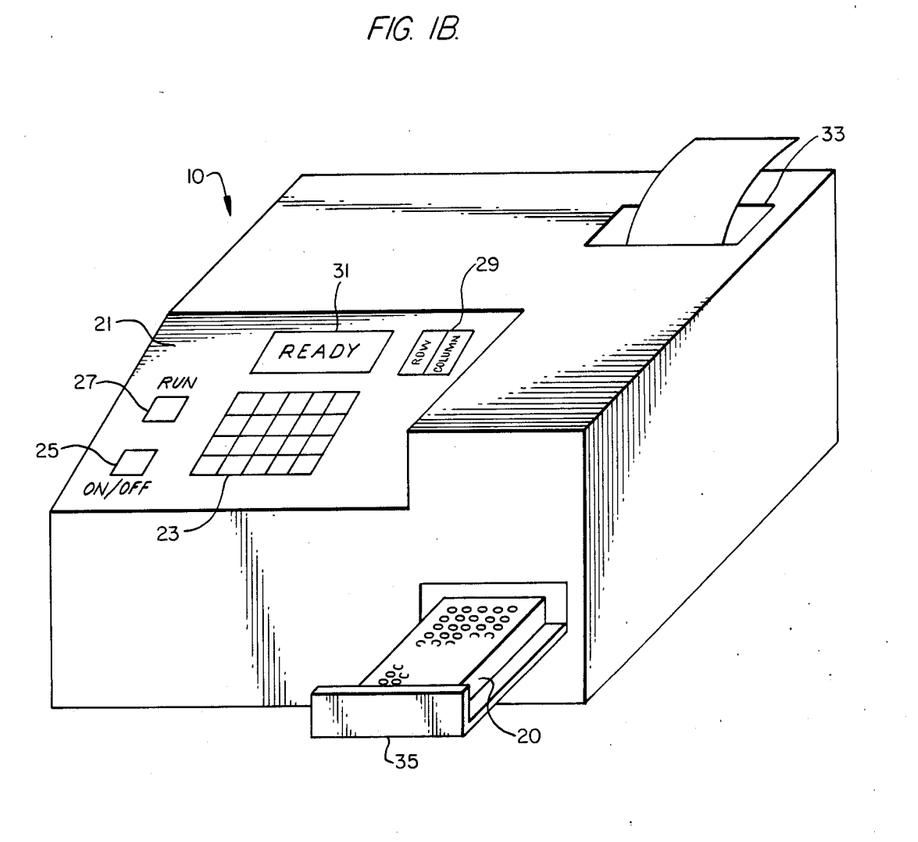
FIG. 1B is a perspective view of another embodiment of fluorescence measuring apparatus of this invention.

Referring to FIG. 1B a second type of housing for an integrated fluorescent immuno assay apparatus 10 is shown. The apparatus 10 includes a control panel 21 which has control buttons 23 for blanking, scanning, wavelength selection, etc. On/off switch 25, run switch 27 and a row/column select display 29 are also included. Also on the panel 21 is a display 31 for display of results as well as prompting the operator concerning the operation of the apparatus. A printer and paper read-out assembly 33 is incorporated in the housing. Finally a microtiter plate 20 can be placed on moveable drawer 35 for insertion into the housing when sample measurement is to begin.

Figure 2:
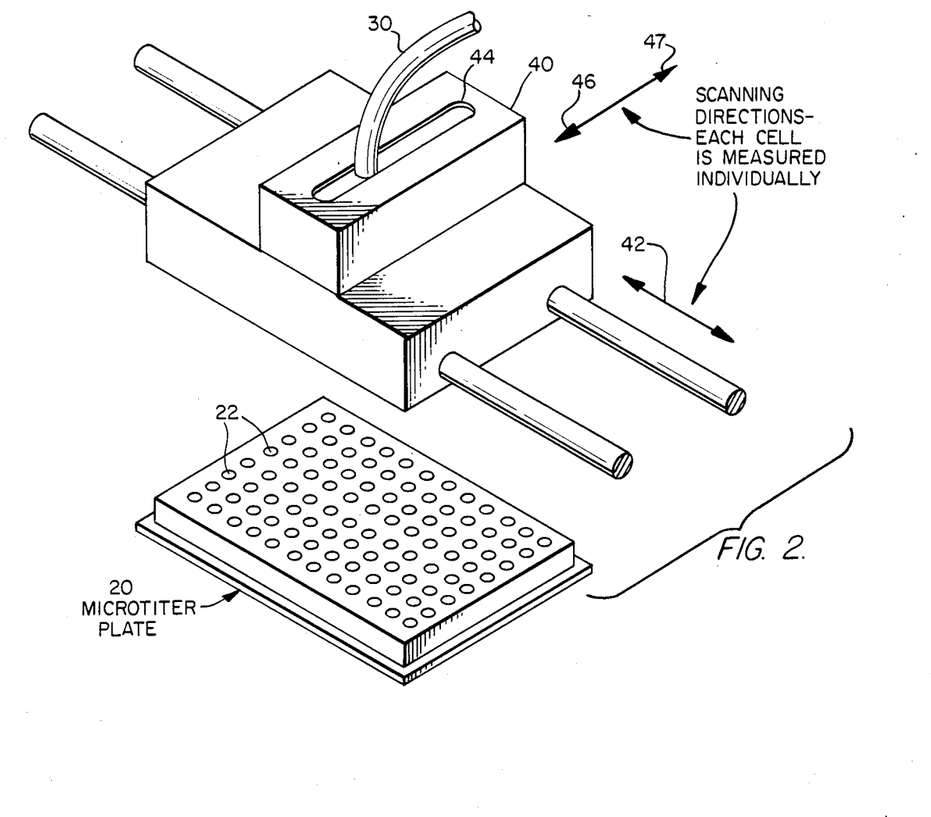
FIG. 2 is a schematic respresentation of the scanning mechanism of the present invention.

Referring now to FIG. 2, scanning mechanism 40 associated with plate 20 is shown. The plurality of wells 22 on microtiter plate 20 are arranged in rows and columns. As here embodied, each row comprises 8 wells. There are twelve rows and a total of 96 wells on the plate. In one mode, microtiter plate 20 is step advanced one row at a time on carrier means 24 by a motor mechanism not shown in this Figure. Plate and 20 is advanced and retracted in the directions indicated by arrows 42. All 96 wells can be measured in a fraction of a minute. In another mode the scanning mechanism 40 can transport the plate 20 to inspect any of the plurality of wells 22 regardless of its location on plate 20.

Fiber optics bundle 30 is connected through slot 44 to the scanning mechanism for scanning each row of wells 22 in the direction shown by arrow 47. Each well 22 in the row of 8 wells is scanned individually by pulsed light energy to excite the substance in the well and the resultant light of emission is detected. After scanning a row the plate 20 is stepped forward to the next row by the carrier mechanism and the scanning mechanism returns in the direction of arrow 46 to begin scanning of the next row. The scanning process is repeated for each row of wells until the fluorescent light of emission from all wells is individually measured.

Figure 3:
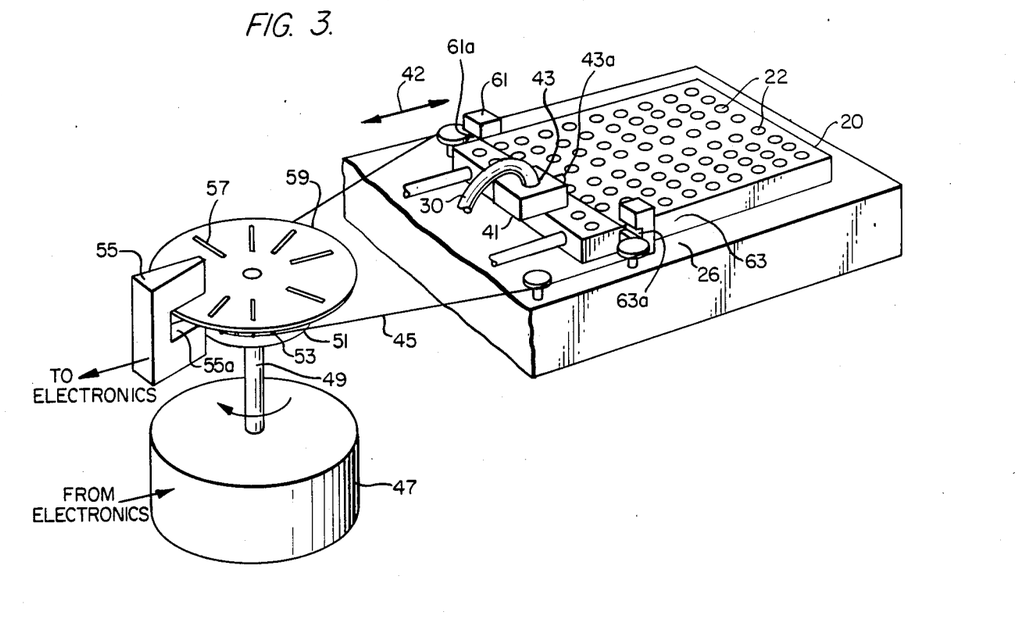
FIG. 3 is a further schematic of the scanning mechanism without the housing.

A detailed discussion of the scanning operation follows in connection with FIG. 3, a schematic showing the advancing and scanning mechanism of the fluorescent immuno assay apparatus. The housing is shown removed from scanning mechanism 40 showing the fiber optics mounting structure 41 on which fiber optics bundle 30 is mounted in cylindrical bearing 43. Bearing 43 allows for movement of bundle 30 as the fiber optics mounting structure 41 is attached to the cable 45 which preferably is steel reinforced and moves with the cable 45. Cable 45 is intermittently driven by motor 47 which causes shaft 49 and pulley 51 to rotate, cable 45 coming in contact with protuberances 53 on the surface of pulley 51 as it moves.

Motor 47 is controlled through electronic controls from LED-photo transistor detector 55. Each time that a slit 57 registers in the slot 55a of detector 55, the LED in the detector is detected by the photo transistor and a signal is generated to cause the motor 47 to stop momentarily. As here embodied eight slots 57 are arranged equidistant around disc 59 causing cable 45 to move intermittently from one to the next of the eight wells 22 in each of the rows of the plate 20, stopping above a well when the next slit 57 registers in the slot 55a of detector 55. The fiber optics bundle 30 stops above each well for a sufficient measurement time to obtain the desired resolution of measurement, the measurement time being adjustable by the operator.

LED-photo transistor detectors 61 and 63 limit the lateral movement of fiber optics mounting structure 43 to the extreme rows of wells 22 on either side of plate 20. Thus when mounting structure 41 reaches the last well, tab 43a moves into slot 61a of detector 61 thereby generating a first control signal to reverse motor 47 and move cable 45 with mounting structure 43 laterally across plate until tab 43a interdicts slot 63a of detector 63. A second control signal is generated stopping motor 47 and the scanning operation is ready to begin again. The first control signal also causes a second motor to move plate 20 the distance of one row along tracks 26 in the direction 42 as the mounting structure 41 returns to begin another lateral scan.

Figures 4, 5A:
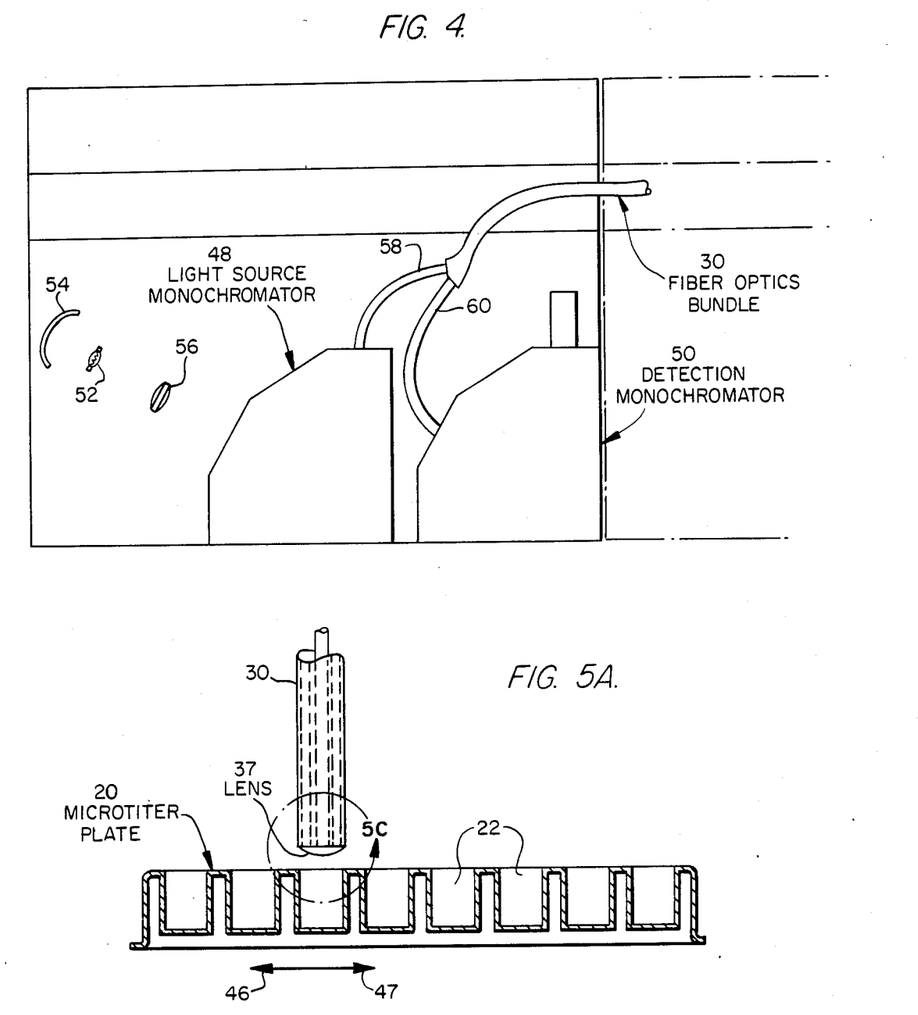
FIG. 4 is a schematic representation of the interior portion of the apparatus shown in FIG. 1 which contains the light source monochromator and the detection monochromator.
FIGS. 5A, 5B and 5C are views of one embodiment of the fiber optics of the present invention.

The interior of the left portion of the fluorescent immuno assay apparatus 10 is schematically shown in FIG. 4. Light source monochromator 48 and detection monochromator 50 are connected through respective fiber light conductors 58 and 60 at one end of fiber optics bundle 30; the other end being connected to the scanning mechanism as discussed above. The monchromator 48 and 50 can be continuously tunable over the operating spectral range of the apparatus. The spectral range can typically include ultraviolet, visible and near infra-red. Double monochromators can also be used in place of the single monochromators to increase the rejection of stray light, or a dual beam monochromator can be used for energy correction in source intensity. Light source conductor 58 and detection conductor 60 are bundled together in this embodiment into fiber optic bundle 30. The light source, shown here as a pulsed xenon lamp 52, is schematically shown with associated optics including mirror 54 and lens 56.

Figure 5B:
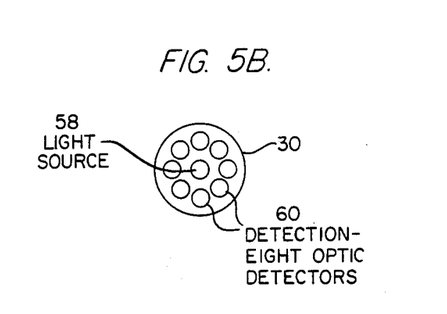
Figure 5C:
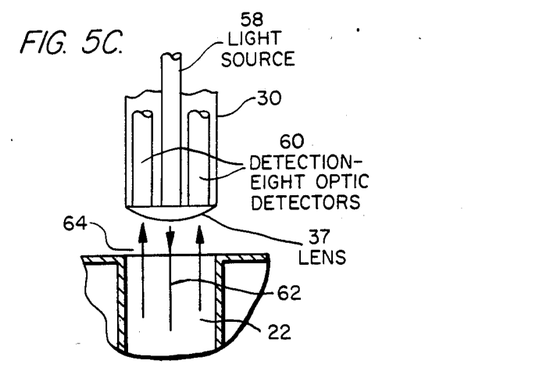

FIGS. 5A, 5B and 5C show details of the front end fluorescent optics as here embodied. In FIG. 5A the scanning relationship between fiber optics bundle 30 and the plate 20 is shown in detail. A cross section of one row of wells 22 of plate 20 is shown scanned by fiber optics bundle 30.

Referring to FIG. 5B, a cross section of the bundle 30, as here embodied, is shown. A central optical conductor or multiple conductors 58 is surrounded by multiple detection optical conductors 60. It will be recognized that other arrangements of the fiber optics bundle can be used as for instance side-by-side single bundles for the light source conductors and the detection conductors or spacial randomization of light source and detection conductors.

As shown in FIGS. 5A and 5B, the front-end fluorescent optics, embodied as fiber optics bundle 30, directs excitation pulsed light energy from light source conductor 58 to the surface of the substance in wells 22 and receives fluorescent emission spectra back along substantially the same path on detection conductors 60, shown in this embodiment as eight conductors. A flat concave lens 37 can be used to focus the exiting and entering light. FIG. 5C is a detail of a portion of FIG. 5A. In FIG. 5C, the excitation light of a specific wavelength is directed from optical conductor 58 orthogonal to the surface of the substance in well 22 as shown by arrow 62. The fluorescent emission of another wavelength is substantially directed along the same path (shown generally by arrows 64) in the opposite direction and is detected by fiber conductors 60. This geometrical arrangement of the beam of exciting light and the direction of viewing the fluorescent light of emission is called front-end optics. With frontal illumination, neither the cuvettes nor plates influence the measurement and the scatter from the excitation wavelength light into the emission analyzer is minimized.

Figure 6:
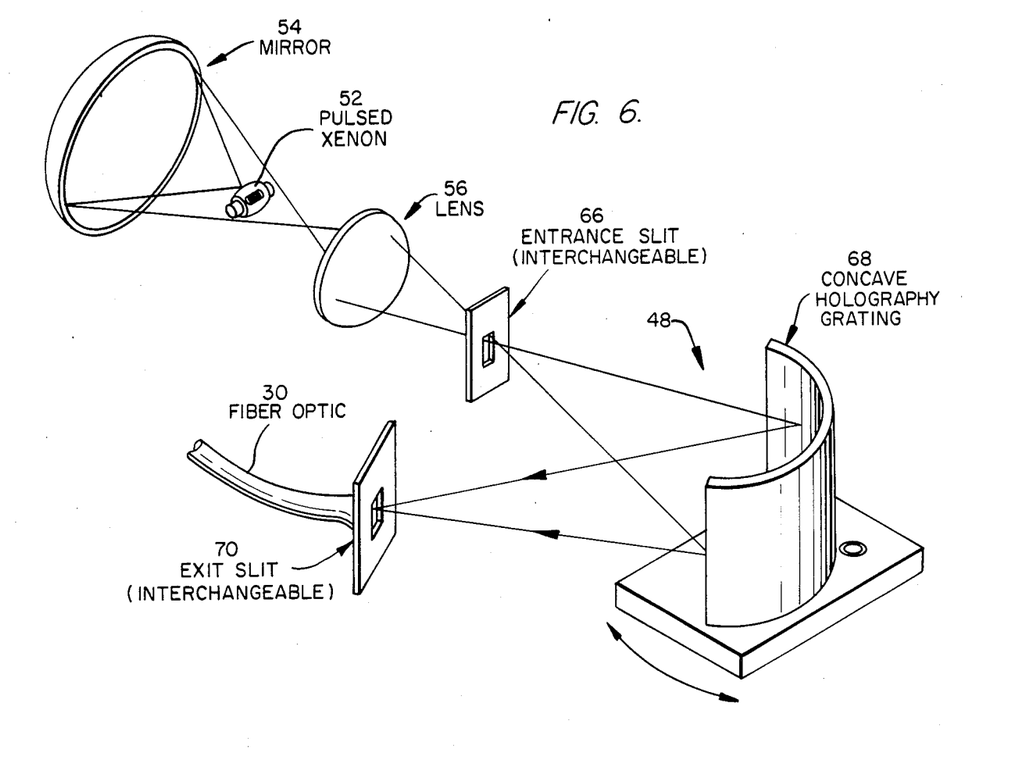
FIG. 6 is a schematic representation of the detection optics.

The light source optics are schematically shown in FIG. 6. As here embodied, pulsed xenon lamp 52 is the light source which is focused through entrance slit 66 by means of mirror 54 and lens 56. Other sources than a xenon lamp can be used. For instance tungsten halogen, mercury and other high pressure gas lamps can be substituted for the xenon lamp.

The source light impinges on concave holographic grating 68 and the wavelength desired is transmitted through exit slit 70 to the source conductor 58 in fiber optics bundle 30. Grating 68 can be rotated to vary the wavelength of the source light which is conducted by source conductor 58. The wavelength resolution of the measurement is continuously adjustable by changing the widths of the slits 66 and 70 in the excitation or emission monochromators or both. An alternative to using continuously adjustable slits is to use a plurality of slits of different widths which can be interchanged depending on the desired resolution.

Figure 7:
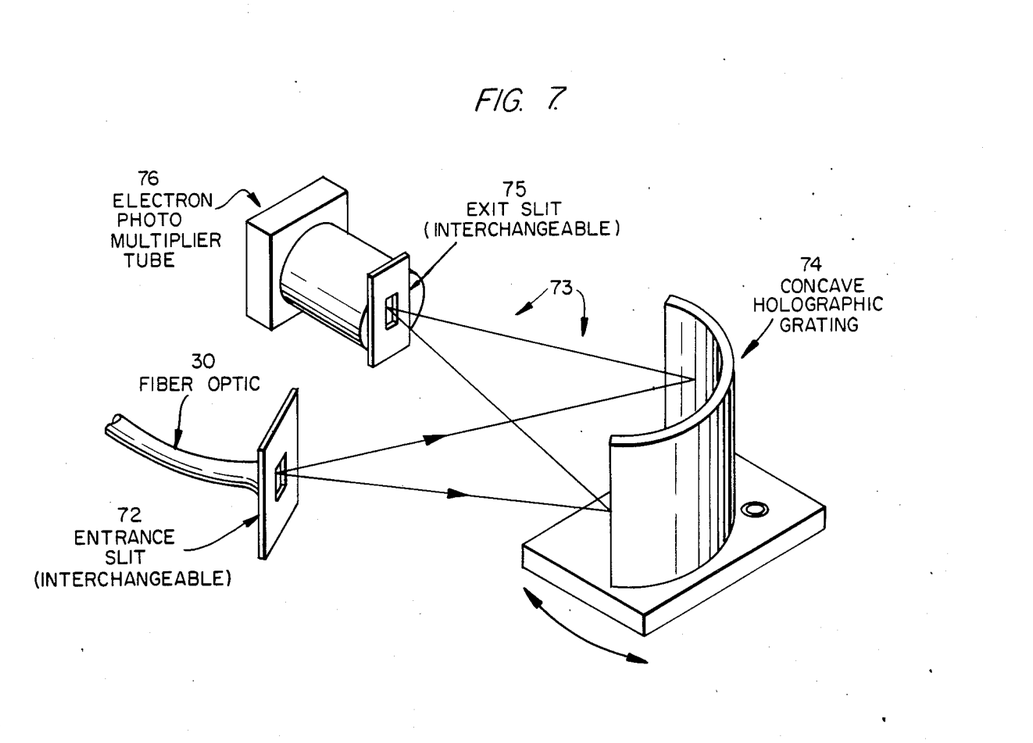
FIG. 7 is a schematic representation of the detection optics.

In FIG. 7, the fluorescent emission optics are shown. The emission light from the substance being measured is directed from fiber optics bundle 30 through entrance slit 72 to emission analyzing means 73. As here embodied the emission analyzing means includes concave holographic grating 74 and electron photomultiplier tube 76. The beam is directed from detection optics detector conductors 60 in fiber optic bundle 30 to concave holographic grating 74. Holographic grating 74 which is rotatable directs the beam to exit slit 75 to impinge on electron photomultiplier tube 76. The intensity of fluorescent emission spectra is detected by the electron photomultiplier tube 76. It will be understood that various analyzers can be used to detect the fluorescent emission spectra. For instance, if sensitivity is not so important, a solid state detector such as a silicon detector or silicon array detectors could be used in place of the photomultiplier tube 76 at a lower cost.

Figure 8:
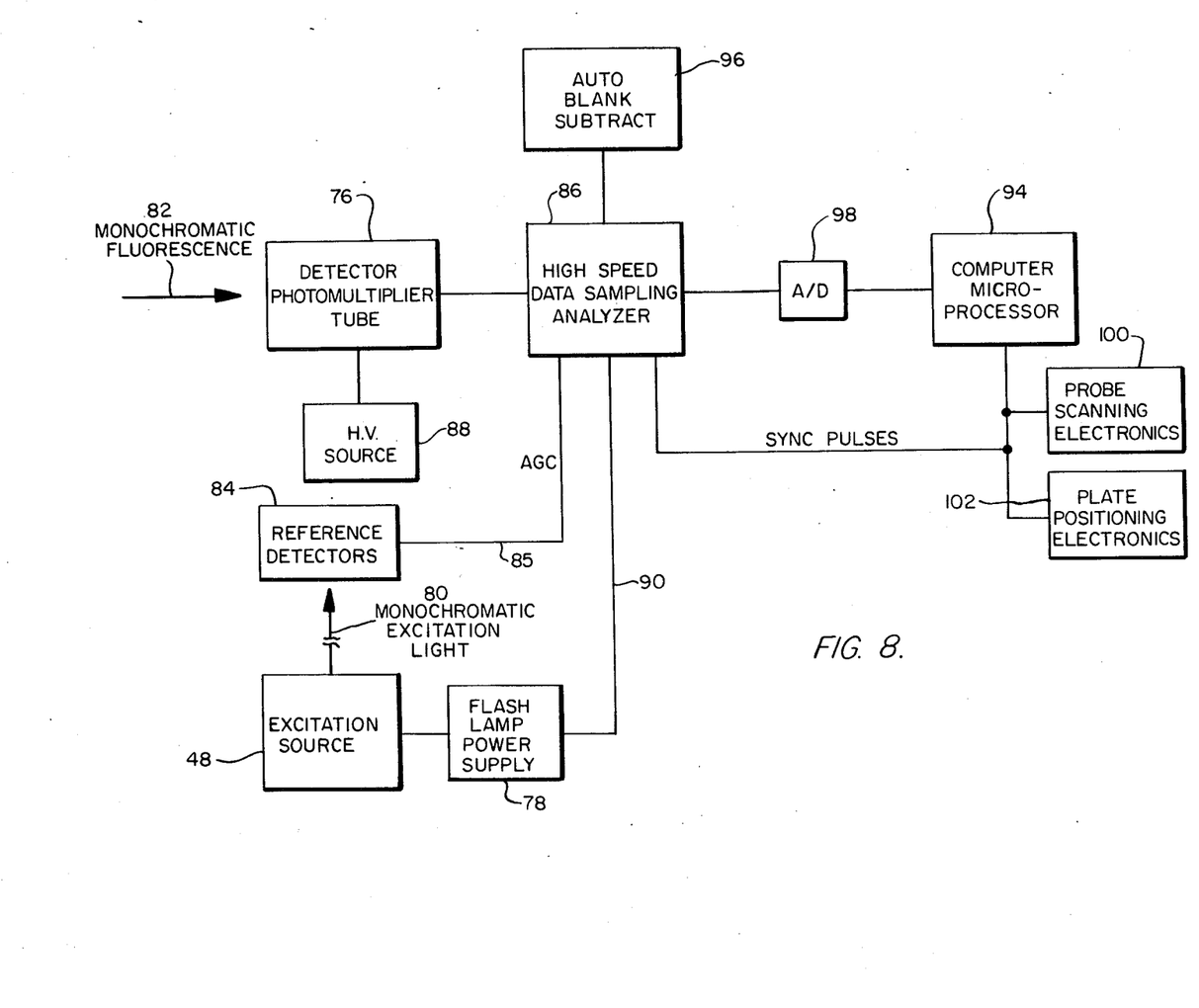
FIG. 8 is a block circuit diagram of the electronics of the fluorescence measuring apparatus of the present invention.

Referring now to FIG. 8 the electronics of the fluorescence immuno assay apparatus will be described. Excitation source 48 powered by flash lamp power supply 78 produces excitation light 80 of a selected wavelength. Excitation light beam 80 is used to scan the wells 22 of the microtiter plate 20 from which monochromatic fluorescence 82 is emitted. To provide automatic gain control, reference detectors 84 are also subjected to monochromatic excitation light 80. Automatic gain control is applied to the high speed data sampling block 86 on line 85 from reference detectors 84, in conjunction with light intensity measured by detector photo multiplier tube 76. The reference detectors 84 are used to compensate for variations in lamp intensity as well as for other temporal variations in the excitation source.

Monochromatic fluorescent emission 82 is detected by spectra emission analyzing means here shown as photomultiplier tube 76 which is powered by high voltage source 88. A solid state detector or detector arrays (such as silicon) or other optical detector can be substituted for the photomultiplier tube. The output of the photomultiplier tube 76 is sampled by the high speed data sampling analyzer 86 in accordance with a trigger pulse supplied from flash lamp power supply 78. Thus the trigger pulse supplied on line 90 allows sampling of each well in the row of microtiter plate 20. The output of the high speed data sampling analyzer 86 is supplied to the A/D converter 98 and then to processor 94.

The auto blank subtract means 96 increases the dynamic range of sample measurement by subtracting background flourescence from the sample measurement. In the embodiment of FIG. 3 some wells 22 in plate 20 are used as blank control. Only the background solution for the sample measurement is measured in these wells. These measurements are then directly applied to the high speed data sampling, analyzer 86 to provide an auto subtract of background fluorescence, and in doing so an increased dynamic range for sample measurement is realized.

Further, signals are supplied from processor 94 to the probe scanning electronics 100 and the plate positioning electronics 102 to cause the scanning of each row of the plate 20 and the row-by-row step advance of the microtiter plate, respectively.

The apparatus described above can also be adapted to measure fluorescence life time, phosphorimetry and polarization measurements. The fluorescence life time of the material analyzed is measured after a single light pulse excites the substance. The fluorescence phenomena is then detected and the decay time measured.

Compensation for background noise can be achieved by a dark subtract process using the microprocessor 94. The microprocessor 94 receives two readings for each sample—one reading with the light on and one with the light off, it subtracts the two thus eliminating background noise, stray light and all drift effects from the measurement.

What is claimed is:

1. A fluorescence measuring apparatus for identifying a substance including:
   excitation means for producing light energy;
   carrier means for holding a plurality of samples which include said substance during excitation scanning of said samples;
   front-end fluorescent optics for directing said excitation light energy on a path orthogonal to the surface of said substance and for receiving fluorescent emission spectra back along substantially the same path from said substance;
   means for scanning said front-end fluorescent optics from sample to sample of said plurality of said samples which include said substance; and
   spectra emission analyzing means for receiving fluorescent emission spectra from said excited samples which include said substance through said front-end fluorescent optics, said emission analyzing means having means for detecting light intensity at the measured wavelength of said fluorescent emission spectra.

2. The fluorescence measuring apparatus of claim 1 wherein said excitation means is a pulsed xenon lamp.

3. The fluorescence measuring apparatus of claim 1 wherein said carrier means is a plate having a plurality of wells adapted for holding samples which include said substance.

4. The fluorescence measuring apparatus of claim 3 wherein said scanning means causes said front-end fluorescent optics to move orthogonal to the direction of said movement of said carrier means while scanning each row of said plate.

5. The fluorescence measuring apparatus of claim 1 wherein said front-end fluorescent optics includes a fiber optics bundle comprised of source light conductors and detection light conductors.

6. The fluorescence measuring apparatus of claim 5 wherein said fiber optics bundle includes a central light source conductor surrounded by a plurality of detector light conductors.

7. The fluorescence measuring apparatus of claim 5 further including a lens for focusing the exiting and entering light from and to said fiber optics bundle.

8. The fluorescence measuring apparatus of claim 1 wherein said excitation means is a light source monochromator and said emission means is a detection monochromator.

9. The fluorescence measuring apparatus of claim 8 wherein said detection monochromator is tunable continuously over the operating spectral range.

10. The fluorescence measuring apparatus of claim 8 wherein said excitation monochromator is tunable continuously over the operating spectral range.

11. The fluorescence measuring apparatus of claim 8 wherein the light source monochromator includes exit and entrance slits the width of which are adjustable thereby providing adjustable wavelength bandpass.

12. The fluorescence measuring apparatus of claim 8 wherein the detection monochromator includes exit and entrance slits the width of which are adjustable thereby providing adjustable wavelength bandpass.

13. The fluorescence measuring apparatus of claim 8 wherein emission analyzing means further includes an electron photomultiplier tube.

14. The fluorescence measuring apparatus of claim 8 wherein said emission analyzing means further includes a solid state detector.

15. The fluorescence measuring apparatus of claim 1 further including reference detector means for compensating light intensity variations of said excitation means.

16. The fluorescence measuring apparatus of claim 1 wherein said scanning means transport said front-end fluorescent optics to any one of said plurality of samples held by said carrier means.

17. The fluorescence measuring apparatus of claim 1 wherein said scanner means can be adjusted to vary the measurement time for each sample.

18. The fluorescence measuring apparatus of claim 1 wherein said spectra emission analyzing means includes a microprocessor and a high speed sampling analyzer, said microprocessor being adapted to receive signals indicative of received fluorescent emission spectra from said high speed sampling analyzer.

19. The fluorescence measuring apparatus of claim 18 wherein said microprocessor processes said signals to subtract background noise and stray light effects from the measurements made for each sample.

20. The fluorescence measuring apparatus of claim 1 further including auto blank subtract means applied to the light intensity detecting means for subtracting background fluorescense from the sample fluorescence.

21. A fluorescence measuring apparatus for identifying a substance including:
   excitation means for producing light energy;
   carrier means for holding a plurality of samples which include said substance during excitation scanning of said samples;
   front-end fluorescent optics for directing said excitation light energy on a path orthogonal to the surface of said substance and for receiving fluorescent emission spectra back along substantially the same path from said substance;
   means for scanning said front-end fluorescent optics from sample to sample of said plurality of said samples which include said substance; and
   fluorescence and phosphorescence life time measuring means for receiving fluorescent emissions from said excited samples which include said substance through said front-end fluorescent optics to determine the life time of said fluorescent phenomena.

22. Apparatus for fluorometric analysis of samples containing a substance comprising:
   means for emitting a tunable, substantially monochromatic beam of radiation;

first fiber optic means for conducting said beam to a container of a sample to be analyzed;
lens means on one end of said fiber optics means for focusing said beam on the surface of said sample in said container;
second fiber optics means for detecting fluorescent radiation emitted by said substance;
said second fiber optics means being aligned with said first fiber optics means such that the radiation incident on said sample is substantially parallel to the emitted radiation detected by said second fiber optic means; and
means optically connected to said second fiber optic means for measuring the intensity of particular wavelength components of the emitted fluorescent radiation.

* * * * *